United States Patent
Lopez et al.

(10) Patent No.: US 7,285,282 B2
(45) Date of Patent: Oct. 23, 2007

(54) MUCIN PEPTIDE WITH IMMUNOENHANCING PROPERTIES

(75) Inventors: Diana M. Lopez, Miami, FL (US);
Lynn M. Herbert, Miami, FL (US);
Mantley Dorsey, Jr., Miami, FL (US);
Günter Kraus, Miami, FL (US); H. James Hnatyszyn, Miami, FL (US)

(73) Assignee: University of Miami, Miami, FL (US)

( * ) Notice: Subject to any disclaimer, the term of this patent is extended or adjusted under 35 U.S.C. 154(b) by 19 days.

(21) Appl. No.: 10/113,800

(22) Filed: Apr. 2, 2002

(65) Prior Publication Data

US 2003/0166853 A1 Sep. 4, 2003

Related U.S. Application Data

(60) Provisional application No. 60/280,137, filed on Apr. 2, 2001.

(51) Int. Cl.
*A61K 47/00* (2006.01)
*A61K 39/00* (2006.01)
*A61K 35/12* (2006.01)
*A61K 38/00* (2006.01)

(52) U.S. Cl. ............................... 424/278.1; 424/280.1; 424/277.1; 424/573; 424/185.1; 514/2; 530/300

(58) Field of Classification Search ................ 530/300, 530/350, 806, 828, 854, 327; 424/185.1, 424/193.1, 278.1, 279.1, 277.1, 573, 280.1
See application file for complete search history.

(56) References Cited

U.S. PATENT DOCUMENTS 5,861,381 A * 1/1999 Chambon et al. ............. 514/44

FOREIGN PATENT DOCUMENTS

WO  WO 92/07000  4/1992

OTHER PUBLICATIONS

Smorodinsky et al. Biochem. Biophys. Res. Commun. 228: 115-121, 1996.*
Kumar et al. J. Immunol. 148: 1499-1505, 1992.*
Bennett et al. Cancer Res. 43: 4183-4190, 1983.*

* cited by examiner

*Primary Examiner*—S. Devi
(74) *Attorney, Agent, or Firm*—Venable, LLP; Ann S. Hobbs (57) ABSTRACT

An isolated peptide or polypeptide containing the sequence VSIGLSFPMLP (SEQ ID NO:1), found in the secreted form of human MUC1, that enhances an immune response when administered to a mammal, compositions containing the peptide, host cells producing the peptide and methods of use. The peptide or polypeptide may be conjugated to a carrier protein and administered as part of a vaccine or immunogenic composition for prevention or treatment of a disease or disorder.

5 Claims, 10 Drawing Sheets

*Renal Cell Carcinoma

Figure 7

*Osteosarcoma

SEQUENCE LISTING

```
<160> NUMBER OF SEQ ID NOS: 1

<210> SEQ ID NO 1
<211> LENGTH: 11
<212> TYPE: PRT
<213> ORGANISM: Homo sapiens

<400> SEQUENCE: 1

Val Ser Ile Gly Leu Ser Phe Pro Met Leu Pro
1               5                   10
```

MUCIN PEPTIDE WITH IMMUNOENHANCING PROPERTIES

This application claims the priority of U.S. provisional application No. 60/280,137, filed Apr. 2, 2001, which is incorporated herein in its entirety. The invention disclosed and claimed in this patent application was supported in part by grant RO1CA25583 from The National Cancer Institute. The U.S. Government has certain rights in the invention.

BACKGROUND OF THE INVENTION

1. Field of the Invention

The invention relates to a mucin peptide with immunoenhancing properties, pharmaceutical compositions containing the peptide, and methods of treating or preventing cancer.

2. Background Information

The MUC1 gene is expressed in normal epithelium and several types of human cancers and at very high levels in breast tumors (1). A major product of this gene is a polymorphic type 1 transmembrane molecule consisting of a large, heavily glycosylated extracellular domain, a transmembrane domain, and a 72 amino acid cytoplasmic tail (2). The polymorphism mainly derives from variations in the numbers of a 20 amino acid tandem repeat unit present in the extracellular domain. A secreted MUC1 isoform (MUC1/sec) (3) has also been found, that includes a sequence of intron 2, terminates prematurely at a stop codon within this intron, and is therefore devoid of the transmembrane domain.

MUC1 and fragments and derivatives thereof have been widely studied for possible use in anticancer vaccines and cancer therapy. U.S. Pat. No. 6,344,203 discloses peptides that mimic MUC1 and bind to IB4 lectin and anti-Gal.alpha.(1,3)Gal antibodies, for use in a cancer vaccine. The peptides are conjugated to carrier proteins such as tetanus toxoid, diphtheria toxoid or oxidized KLH in order to stimulate T cell help.

U.S. Pat. No. 5,827,666 discloses a synthetic MUC1 peptide comprising at least two 20-amino acid tandem repeats of MUC1 that is capable of attaining native conformation in the absence of glycosylation. The synthetic peptide is indicated to be useful, inter alia, in a vaccine that also includes an amino acid sequence for an epitope. U.S. Pat. No. 5,989,552 discloses a conjugate of a MUC1 polypeptide or tandem repeats thereof and oxidized mannan, for use in immunotherapy.

U.S. Pat. No. 6,080,725 discloses saponin analog adjuvants that may be utilized with MUC1 and peptide fragments thereof as tumor-associated antigens in a vaccine.

MUC1 has also been described and used as a cancer cell determinant or marker, as disclosed, for example, in published U.S. patent application Ser. Nos. 20020009759, 20020012931, 20020022235, and 20010051351.

In the aforementioned disclosures, MUC1, and fragments and mimics thereof are utilized as or considered to be tumor-associated antigens for use in vaccines or immunogenic compositions, or as markers for diagnostic tests.

In the present invention the unexpected discovery was made that a variant secretory isoform of MUC1 has the properties of an adjuvant, and thus has immunoenhancing properties that are distinct from those of an antigen.

SUMMARY OF THE INVENTION

A peptide including the amino acid sequence VSIGLSFPMLP (SEQ ID NO:1), and analogs and derivatives thereof, demonstrates immunomodulatory activity in vivo. Such peptides and the nucleic acids (e.g., RNA, DNA) encoding them may be used as adjuvants to stimulate or otherwise enhance an immune response in a subject, animal or human, as assayed by humoral or cellular criteria known in the art. For example, the enhancement of antibody production, secretion of their soluble immune mediators (e.g., cytokines), antigen presentation, effector cell production or functions (e.g., cytotoxicity), other known measures of immune response, or a combination thereof, may be used to show efficacy. In particular, the peptides or nucleic acids may be used as vaccine adjuvants, to enhance in vivo immune responses, to induce in vivo and/or in vitro the production of cytokines, as a mitogen of one or more cell subpopulations, or to enhance cellular cytotoxicity. It is one object of the invention to provide a novel molecule for immunomodulation and potentiation.

To stimulate or otherwise enhance an antigen-specific immune response, the peptide may be incorporated into a vaccine formulation with the antigen (e.g., a tumor antigen, or one derived from an infectious agent such as a bacterium, virus, protozoan, fungus, mold or yeast) or conjugated to the antigen. Nucleic acid may be incorporated into a formulation for genetic vaccination with the antigen and/or an expression vector encoding the antigen; or a nucleotide sequence encoding VSIGLSFPMLP (SEQ ID NO:1), or an analog or derivative thereof, may be included in an expression vector ligated to or distinct from a region encoding an antigen. Components of a vaccine formulation such as other adjuvants and/or cytokines may also comprise the formulation. Thus, the compositions may be incorporated into cellular, acellular, fractionated or purified, recombinant, protein based, or "naked DNA" vaccines.

The tumor types that may be treated include, but are not limited to, sarcomas and carcinomas. For example, a cancer such as leukemia, lymphoma or brain cancer may be treated. In general, any antibody-based or other immunological treatment may be enhanced with the invention.

The invention provides an efficacious and less toxic alternative to other adjuvants for enhancement of an immune response. It can be produced under conditions that satisfy standards for biologicals intended for medical or veterinary treatment, and is biocompatible with formulations used for therapy and prophylaxis.

The terms "peptide", "polypeptide" and "protein", as used herein, are interchangeable, and each refers to a sequence of naturally occurring amino acids. In general, "peptide" is intended to refer to a sequence of less than 20 amino acid residues, "polypeptide" to a sequence of 20 or more amino acid residues and as used herein is intended to encompass proteins as well. Preferably, the peptide, polypeptide or protein of the invention comprises between 11 and 200 amino acid residues, more preferably between 11 and 100 residues, even more preferably between 11 and 50 residues, and most preferably 11, 12, 13, 14, 15, 16, 17, 18, 19 or 20 residues.

As used herein, the term "isolated" refers to material removed from its original environment (e.g., for naturally occurring substances, removed from their natural environment). Such material could be part of a vector or a composition of matter, or could be contained within a cell, if said vector, composition or cell is not the original environment of the material.

It is one object of the invention to provide an isolated peptide, polypeptide or protein comprising the amino acid sequence VSIGLSFPMLP (SEQ ID NO:1), or an analog or derivative thereof. The peptide of the invention has immunoenhancing properties and can be used in pharmaceutical compositions and vaccines.

The term "analog", as used herein, is intended to mean a sequence variant having the same or similar functional characteristics (i.e. producing an immunomodulatory effect). Such variants may have a single or several (2-3) substitutions of amino acid residues, preferably conservative substitutions, such that the variant retains the immunomodulatory characteristics of the "parent" compound.

The term "derivative", as used herein, is intended to mean a peptide, polypeptide or protein comprising sequence VSIGLSFPMLP (SEQ ID NO:1) that has been modified by the addition of at least one additional group and that retains the immunomodulatory ability characteristic of the parent compound. In a preferred embodiment, the derivative comprises a KLH molecule to which multiple copies of the peptide of the invention that are conjugated. The derivative may also be an antigen to which the peptide, polypeptide or protein of the invention is attached. Other examples of derivatives include, but are not limited to, OVA and BSA conjugated to multiple copies of the peptide. The peptide should also be useful in its pure form. The peptide, polypeptide or protein of the present invention may be produced by conventional methods of chemical synthesis or by recombinant DNA techniques. For example, a host microorganism may be transformed with a DNA fragment encoding the polypeptide and the polypeptide harvested from the culture. The host organism may be, for example, a bacterium, a yeast, a viral vector, or a mammalian cell, whereby the DNA fragment in question is integrated in the genome of the host organism or inserted into a suitable expression vector capable of replicating in the host organism. The DNA fragment is placed under the control of regions containing suitable transcription and translation signals. Methods for obtaining polypeptides by these means are familiar to persons skilled in the art.

It is another object of the invention to provide a nucleic acid encoding the peptide, polypeptide or protein of the invention, or derivative or analog thereof The nucleic acids of the invention may be produced recombinantly, synthetically, or by any means available to those of skill in the art, and may be cloned using techniques known in the art. In this regard, the invention also includes a vector comprising the nucleic acid of the invention, and a host cell comprising the nucleic acid of the invention.

As used herein, the terms "nucleic acid" "oligonucleotide", and "polynucleotide" are intended to include RNA, DNA, or RNA/DNA hybrid sequences of more than one nucleotide in either single chain or duplex form, and are used interchangeably.

The terms "complementary" or "complement thereof", as used herein, refer to sequences of polynucleotides which are capable of forming Watson & Crick base pairing with another specified polynucleotide throughout the entirety of the complementary region. This term is applied to pairs of polynucleotides based solely upon their sequences and does not refer to any specific conditions under which the two polynucleotides would actually bind.

The invention also includes an immunogenic pharmaceutical composition comprising the peptide or polypeptide of the invention, or an analog or derivative thereof, and a pharmaceutically acceptable excipient or carrier. In a preferred embodiment, the pharmaceutical composition includes at least one antigen, preferably a tumor antigen. Tumor antigens include, for example, autologous tumor cells, allogeneic tumor cells, gangliosides, carcinoembryonic antigen, prostate specific antigen, melanoma associated antigens and p53 as well as other tumor antigens familiar to those of skill in the art. Other antigens that may be used in the invention include viral antigens, such as those derived from papillmaviruses, Hepatitis B and C, HIV, and HTLV-1, and antigens derived from bacteria and other infectious microorganisms such as *M. Tuberculosis.*

The invention also includes a vaccine, and a method of inducing or enhancing an immunological response. In a preferred embodiment, the vaccine comprises an immunomodulatory peptide or polypeptide of the invention, or an analog or derivative thereof, an antigen, and a pharmaceutically acceptable excipient or carrier. In a particularly preferred embodiment, the antigen is a tumor antigen.

The formulation of vaccines is generally known to those of skill in the art and is widely described in the technical literature (see, for example, Remington's Pharmaceutical Sciences, 17th ed., Mack Publishing Co., Easton, Pa., USA.)

The immunogenic pharmaceutical composition or vaccine of the invention may also include one or more additional adjuvants, such as BCG, KLH, IL-2, GM-CSF and cytoxan, which may be optionally linked to the immunomodulatory peptide or polypeptide of the invention. In one preferred embodiment, the immunomodulatory peptide of the invention is conjugated to KLH with malaimide-activated KLH. A number of linkage packages are known in the art that can be used depending on the adjuvant to which the peptide is conjugated. The general form will be R-HNCO-X or R-HCNO-X where R=adjuvant of choice and X=the peptide.

It is also an object of the invention to provide a method of preventing or treating a disease or disorder by the administration of a safe and effective dose of a vaccine or pharmaceutical composition of the invention. Safe and effective dosages of the pharmaceutical compositions and vaccines of the invention can be determined by persons of skill in the art without undue experimentation. A safe and effective dosage is considered to be one that can be administered to a subject to produce a beneficial effect on the subject's immune response without causing adverse effects that would be considered unacceptable by persons of skill in the art. It will be appreciated that any such adverse effects must be balanced against the benefits of the treatment of the invention, alternative available treatments, and other factors familiar to those of skill in the art. In a preferred embodiment, the invention provides a method for the prevention or treatment of tumors, particularly cancerous tumors.

DETAILED DESCRIPTION OF THE INVENTION

In order to study the immune responses against a mammary tumor using a defined tumor antigen, we transfected DA-3 cells, a mammary tumor cell line that leads to metastatic lesions and death of BALB/c mice hosts, with the transmembrane MUC1 isoform (DA-3/TM), with the secretory form (DA-3/sec), or with the neomycin vector alone (DA-3/neo). Transfection with the secretory form of MUC1 renders the DA-3 cells incapable of growing in intact BALB/c mice, while they grow in nude BALB/c animals. Vaccination with DA-3/sec cells confers protection to challenge with the DA-3/TM or DA-3/neo cells and against two unrelated tumors also syngeneic to BALB/c mice. It appears that a unique 11 amino acid peptide present in the secreted MUC1 isoform is involved in the protective effect and serves as an immunoenhancer molecule.

Materials and Methods

Mice and Tumors. Intact BALB/c mice were maintained by brother-sister matings in our laboratory at the University of Miami School of Medicine. BALB/c nu+/nu+ were purchased from Taconic Labs. The DA-3 tumor cell line was derived from the in vivo D1-DMBA-3 mammary tumor syngeneic to BALB/c mice (4). The DA-3 cells produce tumors in BALB/c mice and cause metastatic lesions in the lung. The cell line is grown in RPMI-1640 media supplemented with 5% FCS (fetal calf serum), 100 µpenicillin, 100 µg/ml streptomycin, $5 \times 10^{-5}$ M 2-Beta-mercaptoethanol (2-BME), 2 mM L-glutamine, 1% nonessential amino acids, 1% essential amino acids, and 1% sodium pyruvate (all from GIBCO BRL, Gaithersburg, Md.), and maintained by serial passage. These cells are free of endotoxin as ascertained by routine assays with Limulus amebocyte lysate (Pyrogent® plus; Whittaker M. A. Bioproducts, Inc., Walkersville, Md.).

Preparation of peptide fragments and antibodies. The monoclonal antibody designated H23 was used to detect the tandem repeat sequence common to both MUC1/TM and MUC1/sec. Antibody 1709 (Ayes Labs, Tigard, Oreg) was prepared by immunizing chickens with the MUC 1/sec specific peptide VSIGLSFMLP (SEQ ID NO:1) conjugated to KLH with malaimide-activated keyhole limpet hemocyanin (KLH). Free peptide concentrations and conjugations of at least 150 peptide molecules per KLH molecule were utilized for immunization. Pre-immune IgY antibody was prepared from eggs collected prior to immunization.

Transfection of DA-3 cells. Stable transfectants expressing MUC1 isoforms were generated by co-transfecting an expression plasmid harboring either MUC1/TM or the secreted form MUC1/sec cDNA with the neomycin plasmid (pSV2 neo) selection marker into DA-3 mouse mammary tumor cells. As control, cells were also transfected with the empty plasmid and selected for neomycin resistance.

Tumor Growth in vivo. The parental DA-3 cells, the neomycin control and MUC1 isoforms transfected cells were washed, counted, and $10^6$ cells were injected subcutaneously (s.c.) in syngeneic intact or nude (nu$^+$/nu$^+$) BALB/c mice. Tumor growth was monitored every 2-3 days and mice bearing a tumor of >10 mm as measured with a caliper were scored as tumor positive.

Vaccination Protocols. BALB/c mice were vaccinated two or three times two weeks apart with $10^6$ DA-3/sec tumor cells in a physiological saline solution. Two weeks after the last vaccine administration the animals were challenged with DA-3 cells untransfected or transfected with neomycin vector alone or with the MUC1 transmembrane isoform. In some experiments the tumors used to challenge were the renal cell carcinoma, RENCA, or the osteosarcoma K7. $10^6$ tumor cells were used for each challenge mixed with $10^6$ DA-3/sec cells.

In other studies the unique 11 amino acid peptide present in the secreted MUC1 isoform was synthesized by Aves Labs, Inc. (Tigard, Oreg.) and bound to KLH. Because the exact ratio of peptide to KLH varies with each synthesis; the preparations were normalized to deliver the same amount of peptide in each administration. The KLH peptide was used as a vaccine two weeks apart. Fifty μg of peptide was given to BALB/c mice with complete Freund's adjuvant for the first vaccination. Two weeks later 25 μg of the peptide was administered with incomplete Freund's adjuvant. After two weeks the mice were challenged with $10^6$ DA-3/sec or DA-3/neo cells mixed with 25 μg of peptide with no adjuvant.

In all studies unvaccinated mice were given the same tumor challenge as in the experimental groups to serve as controls. Tumor growth was monitored every two or three days and tumor size was measured by caliper.

EXAMPLE 1

DA-3 mammary tumor cells were transfected as described in Materials and Methods with either the transmembrane and secretory isoforms of the human MUC1. The success of the transfections was proven by staining the cells for the presence of the MUC1 tandem repeat using the $H_{23}$ antibody specific for this sequence (5). The resulting cell lines were used in in vivo experiments to determine the incidence and time of tumor appearance in BALB/c mice. As seen in Table 1, implantation of DA-3, DA-3/neo and DA-3/TM mammary tumor cells into mice gave rise to palpable tumors of approximately the same size by seven days and by 15 days essentially all animals had sizable tumors.

TABLE 1

Incidence and Time of Tumor Appearance in BALB/c Mice

| Tumor Type | Day of Tumor appearance | | | | |
|---|---|---|---|---|---|
| | 7 | 15 | 25 | 37 | 12+ months |
| DA-3 | 32/38 | 38/38 | | | |
| DA-3/neo | 17/25 | 24/25 | 25/25 | | |
| DA-3/TM | 29/36 | 33/36 | 35/36 | 36/36 | |
| DA-3/sec | 0/70 | 0/70 | 1/70 | 1/70 | 1/70 |

Figure 1:
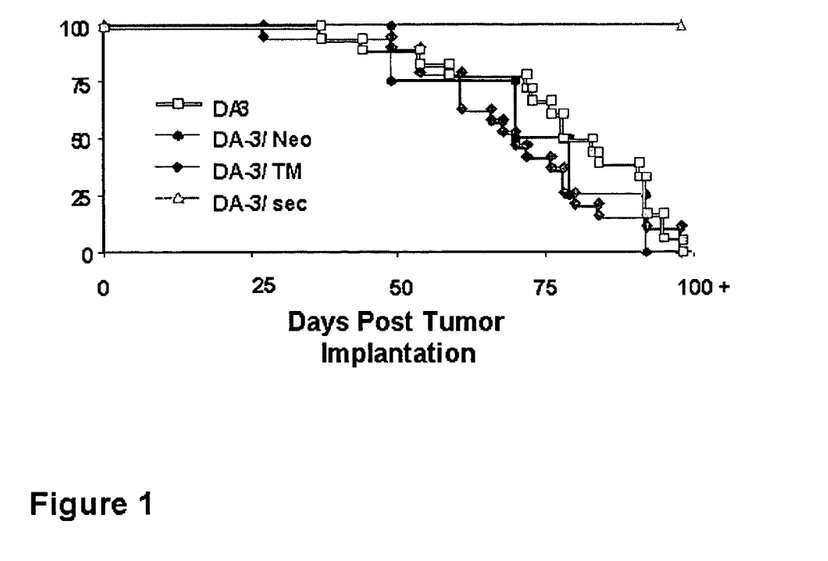
FIG. 1. Survival of intact BALB/c mice after implantation of $10^6$ untransfected DA-3 mammary tumor cells, or with DA-3 cells transfected with the neomycin vector only (DA-3/neo), or with the transmembrane MUC1 isoforn (DA-3/TM) or with the secreted MUC1 isoform (DA-3/sec).

Surprisingly, the DA-3 cells transfected with the MUC1 secreted form (DA-3/sec) failed to cause tumor development. Remarkably, as seen in FIG. 1, these animals remain tumor free even after more than 12 months after implantation, while animals with the other three types of DA-3 cells fail to survive past 100 days. It should be pointed out that no tumor growth was observed in mice that were implanted with the DA-3/sec tumor cells up to a concentration of $1 \times 10^7$ cells per inoculation.

EXAMPLE 2

Figure 2:
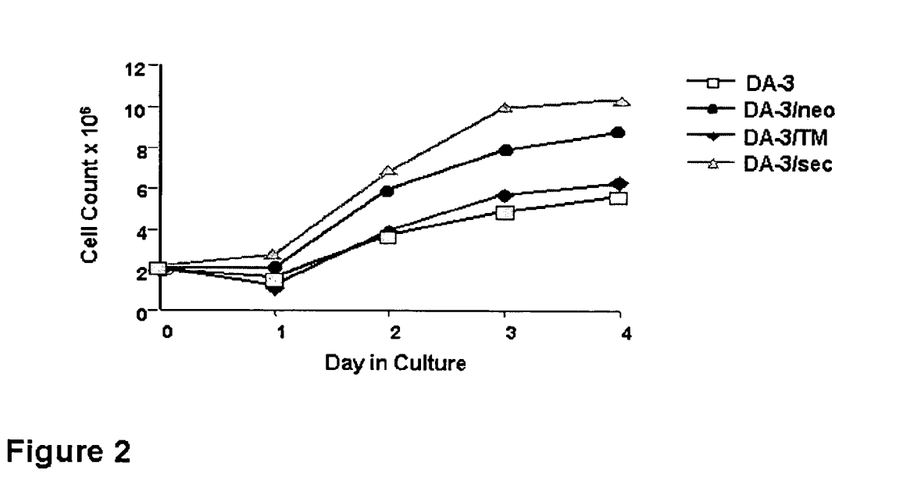
FIG. 2. In vitro growth kinetics of untransfected DA-3 mammary tumor cells or DA-3 cells transfected with the neomycin vector only (DA-3/neo), or with the transmembrane MUC1 isoform (DA-3/TM) or with the secreted MUC1 isoform (DA-3/sec).

A trivial explanation to these results could be that the transfection process had selectively impaired the basic growth potential of the DA-3/sec cells. To test this possibility we investigated the in vitro growth characteristics of the four types of DA-3 tumor cells. As shown in FIG. 2, the parent cell line and all the various transfectants grew with similar kinetics in vitro. In fact, the DA-3/sec cells seemed to proliferate better than the other cell lines, indicating that the in vitro growth potential of these cells has not been altered by the transfection manipulations.

EXAMPLE 3

Figure 3:
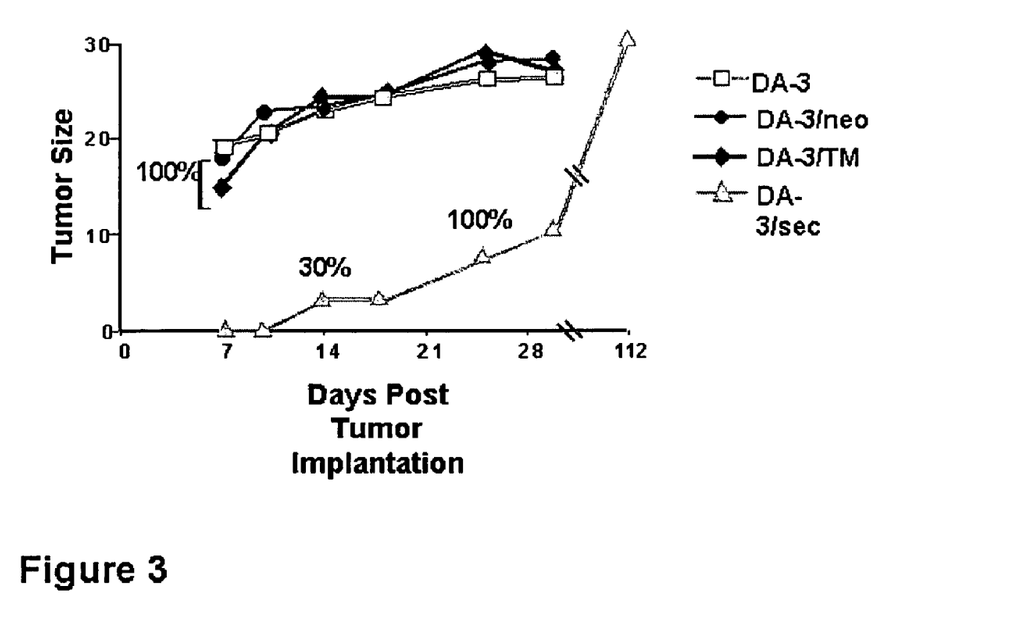
FIG. 3. Growth of tumors in BALB/c ($nu^+/nu^+$) mice that had been implanted with $10^6$ untransfected DA-3 mammary tumor cells, or DA-3 cells transfected with the neomycin vector only (DA-3/neo), or with the transmembrane MUC1 isoform (DA-3/TM) or with the secreted MUC1 isoform (DA-3/sec).

In order to determine whether the DA-3/sec cells had lost all tumorigenic potential in vivo, all four DA-3 cell lines were implanted in $nu^+/nu^+$BALB/c mice and the incidence of tumor appearance and tumor size at various times were assessed. FIG. 3 shows that the DA-3, DA-3/neo, and DA-3/TM cells cause palpable tumors by seven days after implantation in BALB/c nude mice and they grew in a manner similar to that of intact BALB/c animals. In contrast with the results in Table 1 and FIG. 1, DA-3/sec tumor cells gave rise to tumors in 30% of all nude mice by 14 days and by 25 days all these animals had tumors. Thus, the lack of tumor growth in the intact BALB/c mice implanted with the DA-3/sec cells appears to be immunologically controlled, since implantation of this tumor in nude mice resulted in 100% tumor takes, albeit at a slower time of appearance. These results were repeated using other two DA-3 tumor cells separately transfected with the expression plasmid harboring the secreted form of MUC1. As seen in Table 2, none of the three separate DA-3 cells transfections with the MUC1-sec gene were capable of growing in intact BALB/c mice.

TABLE 2

Tumor Incidence of Different DA-3/sec Transfectants in BALB/c Mice

| Transfectant | Incidence |
|---|---|
| DA-3/neo | 6/6 |
| DA-3/TM | 6/6 |
| DA-3/sec | 0/6 |
| DA-3/sec 11 | 0/14 |
| DA-3/sec 22 | 0/11 |

Figure 4:
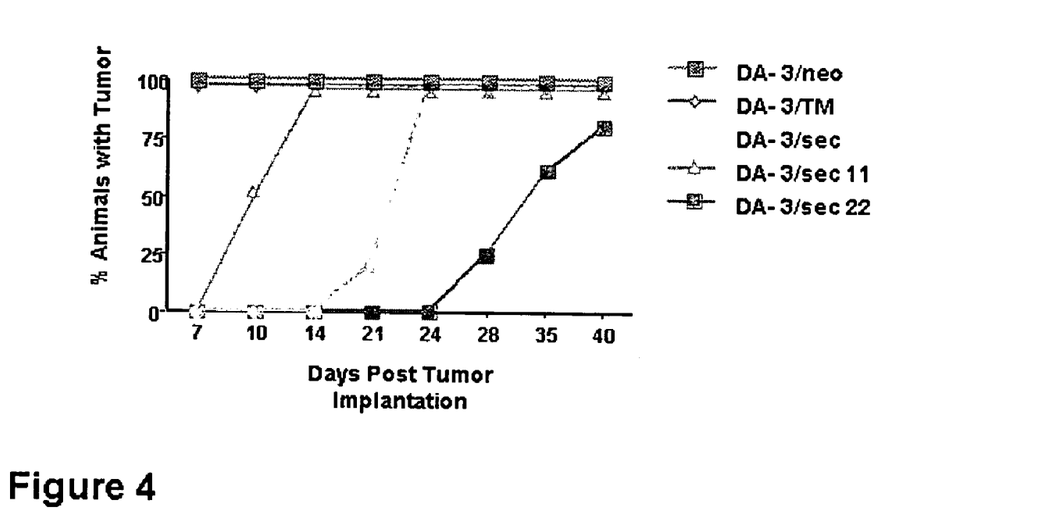
FIG. 4. Tumor growth in nude BALB/c mice after inoculation with $10^6$ untransfected DA-3 mammary tumor cells or with DA-3 cells transfected with the neomycin vector only (DA-3/neo), or with the transmembrane MUC1 isoform (DA-3/TM) or with three separate transfectants of the secreted MUC1 isoform (DA-3/sec).

FIG. 4 shows that the three separate DA-3/sec cell transfectants, i.e. DA-3/sec, DA-3/sec 11, and DA-3/sec 22, could all grow in vivo in BALB/c nude mice, although their growth kinetics in the immunodeficient mice were somewhat different. Interestingly, DA-3/sec tumors that grew in nude BALB/c animals did not grow when implanted in immunologically intact BALB/c mice, but do grow when inoculated with other nude BALB/c animals (data not shown). The results of these experiments suggest that T cells, and to a lesser degree another type of non T cell effector, are involved in the control of growth of tumors transfected with the secreted form of MUC1.

EXAMPLE 4

Figure 5:
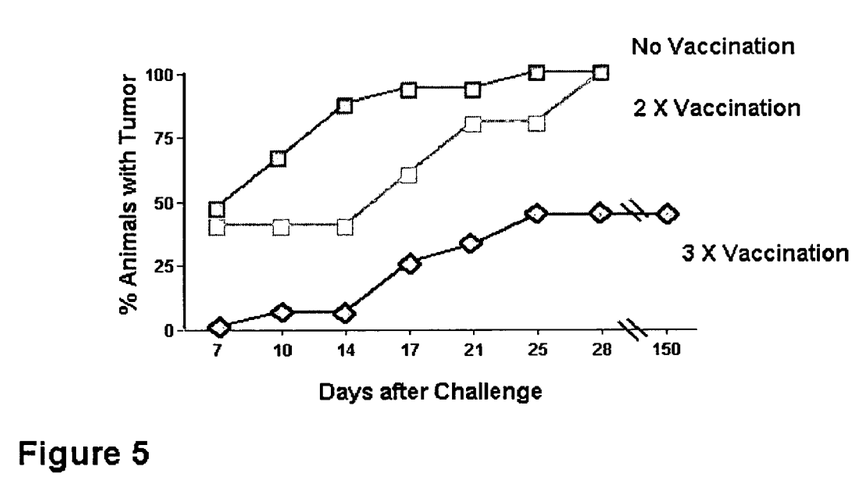
FIG. 5. Effect of vaccination with DA-3 cells transfected with the secreted MUC1 isoform (DA-3/sec) cells on the growth in BALB/c mice of a mixture of DA-3 cells transfected with the transmembrane MUC1 isoform (DA-3/TM) and DA-3 sec cells.
Figure 6:
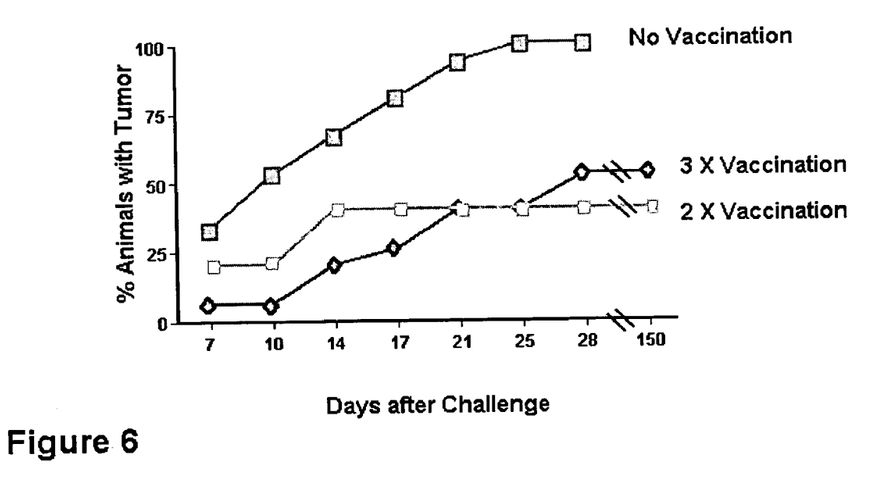
FIG. 6. Effect of vaccination with DA-3 cells transfected with the secreted MUC1 isoform (DA-3/sec cells) on the growth in BALB/c mice of a mixture of DA-3 cells transfected with the neomycin vector only (DA-3/neo) and DA-3 sec cells.

We evaluated whether implantation of BALB/c mice with DA-3/sec cells could confer protection to other MUC1 expressing tumor cells. DA-3 cells expressing no mucin (DA-3/neo) were also included in the study. Experimental groups received two or three injections one week apart of $1\times10^6$ DA-3/sec cells prior to challenge with $1\times10^6$ cells DA-3/TM or DA-3/neo cells alone or mixed with DA-3/sec cells. As controls, unvaccinated animals were challenged with either DA-3/neo or DA-3/TM cells. Animals receiving two injections of unmixed DA-3 sec ($10^6$ cells) caused only a short delay in the appearance of tumors when challenged with DA-3/TM cells alone, i.e. 13/22 animals with tumors at two weeks as compared to 13/14 animals with tumors at one week in the control group. Mice that had received three injections of $10^6$ DA-3/sec cells before challenge unexpectedly retarded the growth of not only DA-3/TM cells but also DA-3/neo cells compared to the unvaccinated control groups. Remarkably, when the DA-3/TM tumor cells used for challenge were mixed with the DA-3/sec cells at the time of implantation (FIG. 5), there was not only a retardation in the time of tumor appearance compared to the control groups, but there was an actual substantial protection resulting in lack of growth of the DA-3/TM tumor cells in 50% of the vaccinated mice. Furthermore, this protection did not appear to be due to a recognition of the MUC1 molecule, since a similar effect could be seen in animals vaccinated with DA-3/sec cells and challenged with a mixture of DA-3/neo and DA-3/sec mammary tumor cells.

EXAMPLE 5

Figure 7:
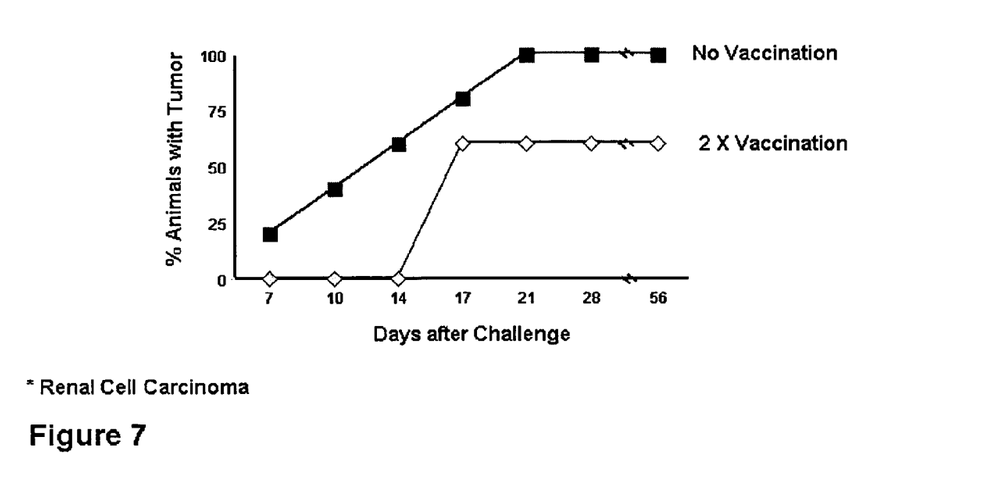
FIG. 7. Effect of vaccination with DA-3 mammary tumor cells transfected with the secreted MUC1 isoform (DA-3/sec cells) on the growth in BALB/c mice of a mixture of the RENCA renal cell carcinoma and DA-3/sec cells.
Figure 8:
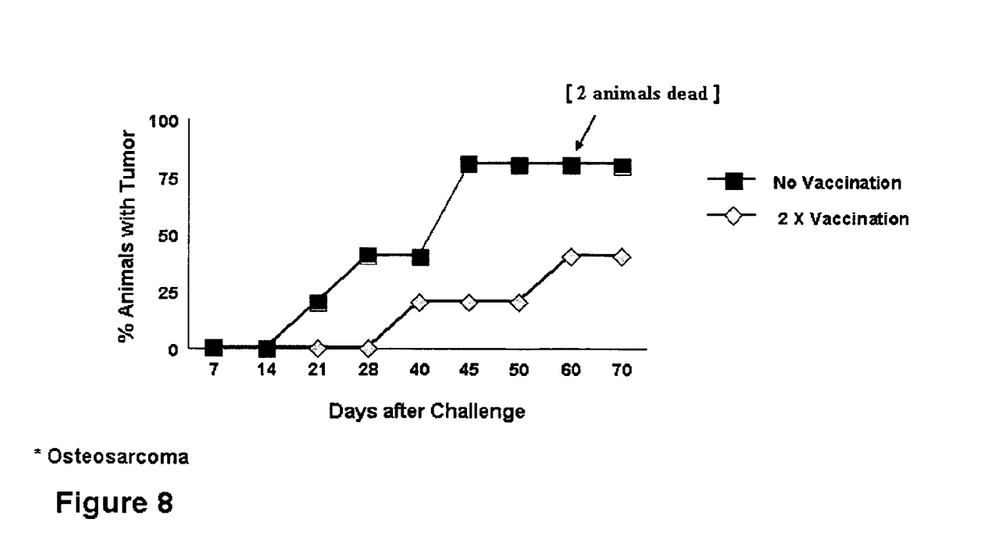
FIG. 8. Effect of vaccination with DA-3 mammary tumor cells transfected with the secreted MUC1 isoform (DA-3/sec cells) on the growth in BALB/c mice of a mixture of K7 osteosarcoma cells and DA-3/sec mammary tumor cells.

Further studies were carried out to determine whether vaccination with DA-3/sec cells could confer protection against the growth of tumors other than those in DA-3 mammary tumor background. Two unrelated tumors syngeneic to BALB/c mice were employed, i.e. a renal cell carcinoma line, RENCA, and an osteosarcoma, the K7 cell line. FIG. 7 shows that vaccination of BALB/c mice twice with the DA-3/sec cells followed by a challenge with a mixture of RENCA cells and DA-3/sec cells resulted in substantial reduction of tumor growth as compared to the unvaccinated controls. The addition of the DA-3/sec at the time of challenge was necessary, as was the case with the DA-3/TM and DA-3/neo cell experiments, since the unmixed RENCA cells growth was not impaired. Similar results were obtained in experiments where the K7 osteosarcoma cells were used. As seen in FIG. 8, 80% of unvaccinated mice implanted with a mixture of K7 and DA-3/sec cells gave tumors appearing by 21 days after challenge. However, mice that had been vaccinated twice with $10^6$ DA-3/sec mammary tumor cells had a delay in tumor appearance to 40 days after challenge and a protection against tumor development. Indeed, 70 days after challenge less than 50% of the vaccinated mice had tumors.

EXAMPLE 6

Figure 9:
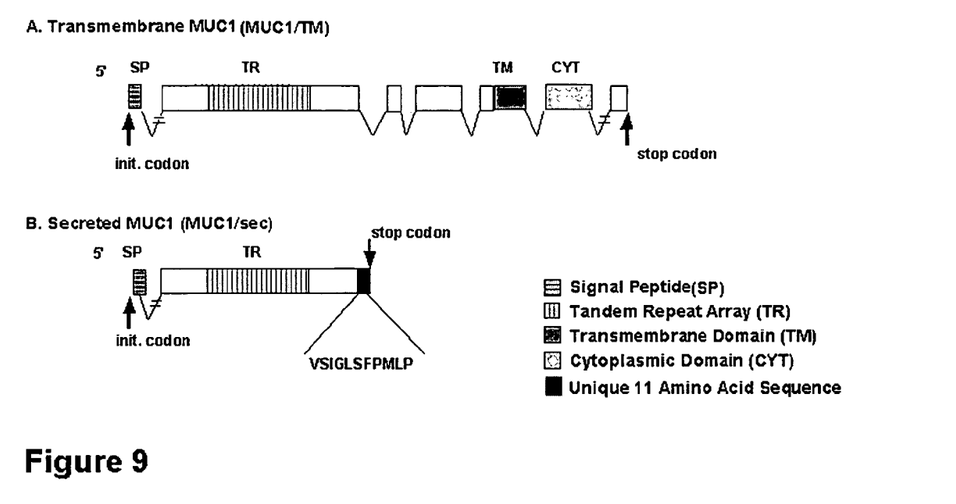
FIGS. 9A and 9B. Schematic representation of the cDNA sequences of the human transmembrane MUC1 (MUC1/TM) and the human secreted MUC1 (MUC1/sec) isoforms comprising VSIGLSFPMLP (SEQ ID NO: 1).

A possible clue about why the secreted form of MUC1 affords protection, was obtained from the analysis of the structures of the MUC1 transmembrane and secreted isoforms. A schematic drawing of the cDNAs from the MUC1/TM and MUC1/SEC isoforms is shown in FIG. 9. The cDNAs are depicted from their 5' termini at the left of the figure. The tandem repeat array is depicted by the barred region and the regions coding for the signal peptide, transmembrane domain, and cytoplasmic domain are indicated by SP, TM, and CYT respectively and have the same shadings in the two forms. The amino acid sequence at the terminal end of the MUC1/sec isoform is VSIGLSFPMLP (SEQ ID NO:1) (3). Importantly, a BLASTP 1.4.11(6) analysis at high stringency of these 11 amino acids revealed approximately 50% identity with the human Ly 49E ligand with no other identity with any known protein sequence. At low stringency there were some similarities with glutathione S-transferase from two *Echinococcus* species, to hypothetical protein MLCB4.30 of *Mycobacterium leprae* and to EF hand protein of two plant species; This peptide is likely to be highly antigenic due to its hydrophilic nature. To ascertain the presence of this peptide in the DA-3 cells transfected with the secreted MUC1 isoform, a chicken IgY antibody against the unique 11 amino acid peptide bound to KLH was prepared. A direct ELISA utilizing this reagent was developed to detect the peptide in the supernatants of DA-3/sec cultures. Briefly, 50 µl of coating buffer containing 0.2-10.0 µg of protein/ml or tissue culture supernatants from serum free cultures were plated overnight at 4° C. Blocking buffer was added for 1 hour at 37° C., plates washed 3 times, primary antibody incubated for 1 hour or overnight; wash 3 times; add secondary antibody, if required, for 1 hour, wash 3 times; add visualization solution; incubate and read. A positive control of purified peptide at known concentrations was employed in all assays. All cultures tested were positive for this molecule (data not shown).

EXAMPLE 7

Figure 10:
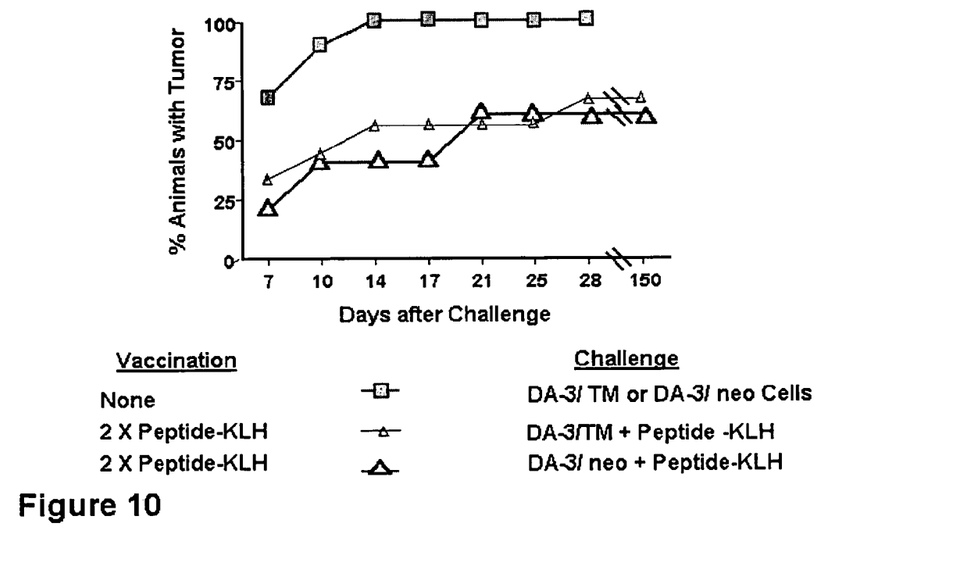
FIG. 10. Peptide vaccination. Effect of vaccination with KLH-bound unique eleven amino acid peptide of the secreted human MUC1 isoform on the growth of a mixture of KLH bound unique peptide with DA-3 cells transfected with either the neomycin vector alone (DA-3/neo) or with the transmembrane MUC1 isoform (DA-3/TM).

Experiments to evaluate the possible beneficial effects of vaccination with this peptide were performed (FIG. 10). Control mice that received injections with DA-3/TM or DA-3/neo cells ($10^6$ cells) resulted in 100% tumor growth whether in the presence or absence of adjuvant alone. Experimental mice received two injections eight days apart with KLH-bound unique peptide in the presence of adjuvant. Eight days after the second injection the animals were challenged with a mixture of KLH bound peptide and tumor cells. Challenge with the peptide mixed with DA-3/TM cells resulted in tumor growth in only 7 out of 12 mice, with an additional animal developing a tumor at 4 weeks. Challenge of vaccinated mice with a mixture of KLH bound peptide and DA-3/neo cells afforded even a greater amount of protection and only 40% of the animals developed tumors, again with one additional mouse showing tumor growth after a month delay. Importantly, the survivor animals have shown no signs of tumor at 6 months after original challenge with either DA-3/TM or DA-3/neo cells.

EXAMPLE 8

Figure 11A:
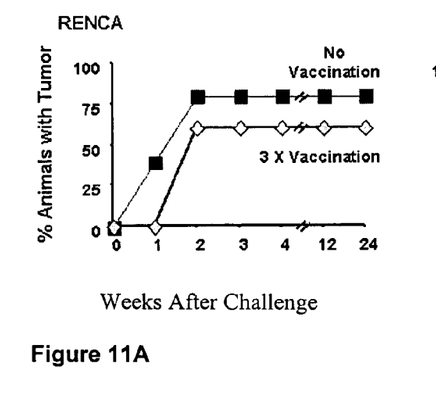
FIGS. 11A and 11B. Effect of KLH-bound unique amino acid peptide from the secreted human MUC1 isoform on the growth of a mixture of KLH bound unique peptide with either RENCA tumor cells in BALB/c mice (11A) or Lewis lung carcinoma on C57/BL6 mice (11B). The figure shows that efficacy of MUC1/sec peptide vaccination is not strain restricted.
Figure 11B:
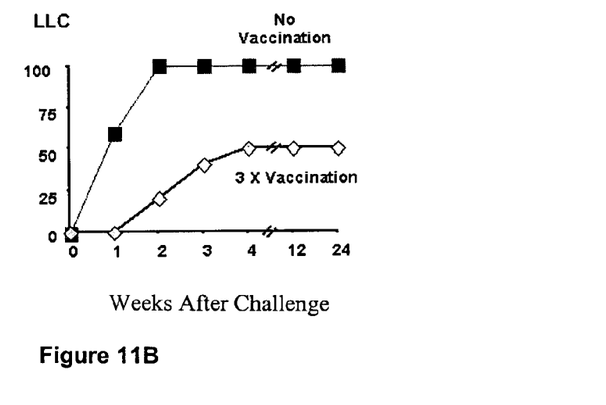

In further studies, the effect of the peptide vaccination was evaluated in two other tumors. In FIG. 11A it can be seen that this protocol gave only a small protection and a retardation of tumor appearance when RENCA cells were implanted in BALB/c mice. Importantly, when the KLH bound immunoenhancing peptide was used in vaccination protocols in another mouse strain (C57/BL6 mice) and challenged with the very aggressive Lewis lung carcinoma, protective effects were also observed, as seen in FIG. 11B.

EXAMPLE 9

Figure 12:
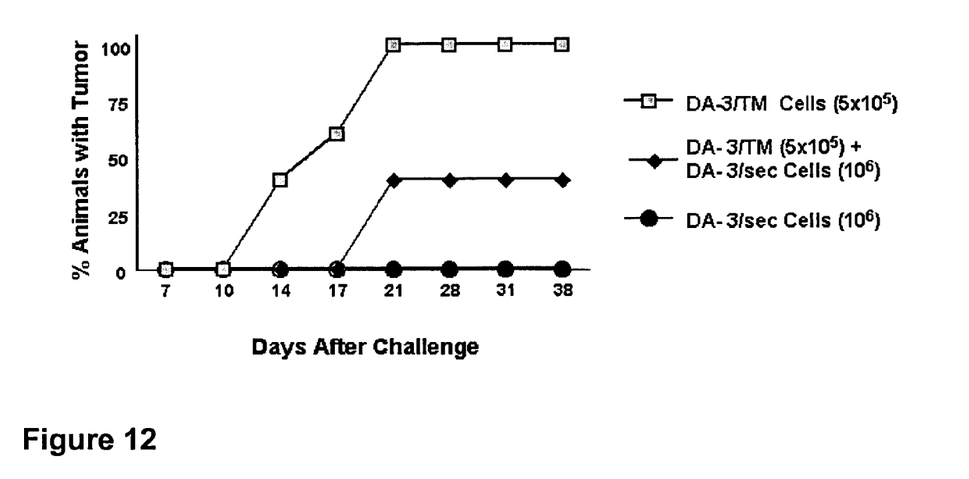
FIG. 12. Effect of administration of a mixture containing a lower number of challenge cells (DA-3/TM) with DA-3/sec cells on tumor growth. The figure shows that a lower number of challenge cells allows effective protection without vaccination.

In order to determine whether a lower number of challenge cells mixed with DA-3 sec cells will obviate the necessity of previous exposure to the latter in order to provide protection against tumor growth, $5\times10^5$ DA-3/TM cells were mixed with an equal amount of DA-3/sec cells and administered to mice. As shown in FIG. 12, this treatment provided 60% protection against tumor development without any previous vaccination.

EXAMPLE 10

Figure 13:
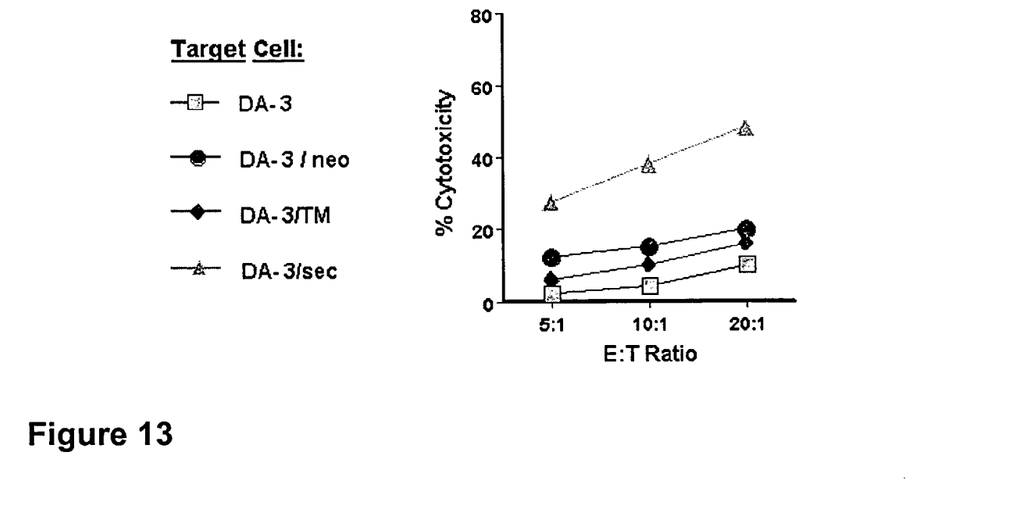
FIG. 13. Cytotoxic activity of spenic cells from DA-3/sec injected mice against DA-3 tumor cell targets.

In order to determine which effector cells are involved in the protection observed against DA-3/sec tumor cell growth, cytotoxicity assays against $^{51}$Cr labeled cells were performed using splenic cells from mice that received an inoculation of DA-3/sec tumor cells two weeks prior to obtaining the cells. $10 \times 10^6$ splenocytes were cultured for 5 days in the presence of $2 \times 10^5 - 2 \times 10^6$ mitomycin-C (MMC) treated DA-3/sec cells. Splenocytes primed with DA-3/sec exhibited a strong cytolytic activity against DA-3/sec cells (FIG. 13). DA-3/sec primed splenocytes have low levels of cytotoxicity against DA-3/TM, DA-3/neo and DA-3 targets. These results suggest that a population of lymphocytes is expanding in vitro upon stimulation with DA-3/sec, which have potent effector function against DA-3/sec targets.

EXAMPLE 11

Figure 14:
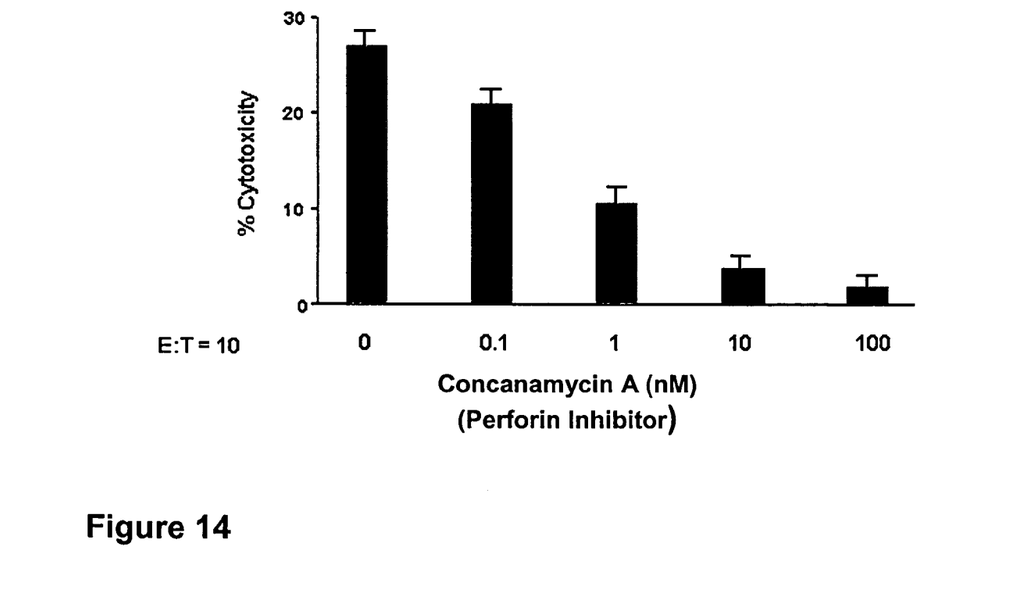
FIG. 14. Effect of perforin inhibitor concanamycin A on cytotoxicity of DA-3/sec splenic cells. Figure shows that perforin mediates lysis of DA-3/sec tumor cells by activated splenocytes.
Figure 15:
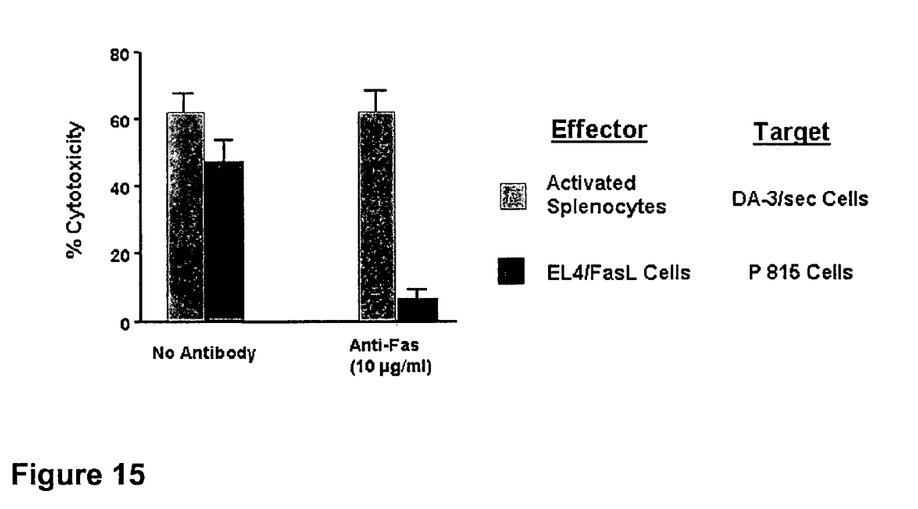
FIG. 15. Effect of anti-Fas antibody on the cytotoxicity of DA-3/sec activated splenocytes against DA-3/sec targets and positive controls. Figure shows that Fas/FasL does not play a role in DA-3/sec cytotoxicity.

Cells of the immune system have multiple mechanisms of killing, which include Fas-Fas ligand interactions (7) and perforin-granzyme mediated killing (8) The DA-3/sec primed splenocytes were treated with anti-Fas antibody or Concanamycin A (CMA), an inhibitor of vacuole acidification through blockage of H$^+$ ATPase that blocks perforin-mediated killing (9). CMA effectively blocked killing of DA-3/sec targets in a dose-dependent manner (FIG. 14), while no effect on cytotoxicity was observed with the addition of the anti-Fas antibody (FIG. 15). These results indicate that Fas/FasL does not play a role in the cytotoxicity of DA-3/sec cells, but that it is mediated through the perforin-granzyme pathway.

EXAMPLE 12

Figure 16:
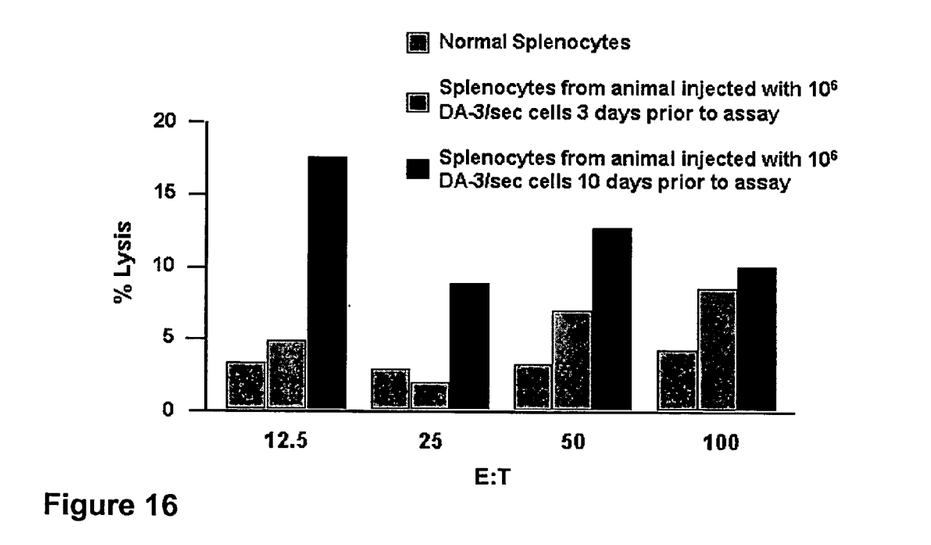
FIG. 16. Effect of in vivo DA-3/sec exposure on classic NK activity against YAC-1 targets. Figure shows that in vivo DA-3/sec exposure results in higher classic NK activity vs YAC-1 targets.

In order to determine whether in vivo exposure to DA-3/sec cells results in higher NK activity against YAC-1 target cells (a classic murine NK-target cell) (10), an experiment was performed in which normal splenocytes were compared with splenocytes that had 3 or 10 day exposure to DA-3/sec cells in vivo with regard to their ability to induce lysis. As seen in FIG. 16, splenic cells from BALB/c mice injected 3 days prior to assay with DA-3/sec cells have somewhat higher levels of lytic activity against YAC-1 cells as compared to those from normal mice. This enhanced NK reactivity is more pronounced in mice that have been inoculated with the DA-3/sec cells 10 days prior testing.

EXAMPLE 13

Figure 17A:
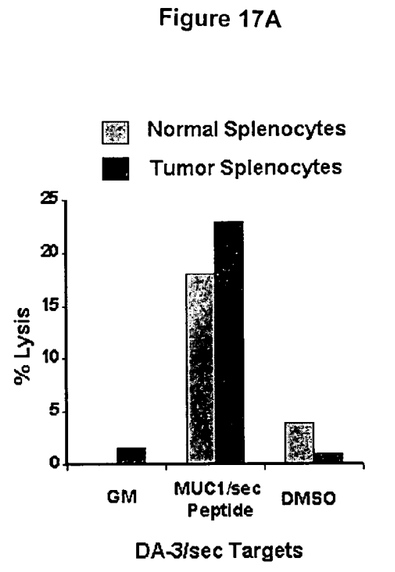
FIGS. 17A and 17B. Effect of MUC1/sec peptide on immune response of D1-DMBA-3 tumor bearers in vitro (17A) and in vivo (17B). Figures show that MUC1/sec peptide stimulates the immune response of D1-DMBA-3 tumor bearers.
Figure 17B:
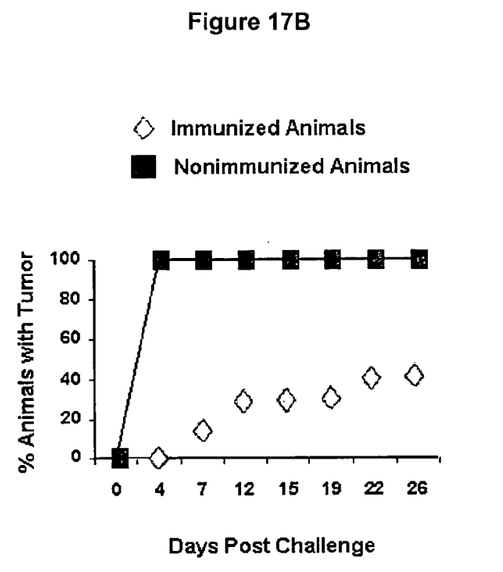
Figure 18A:
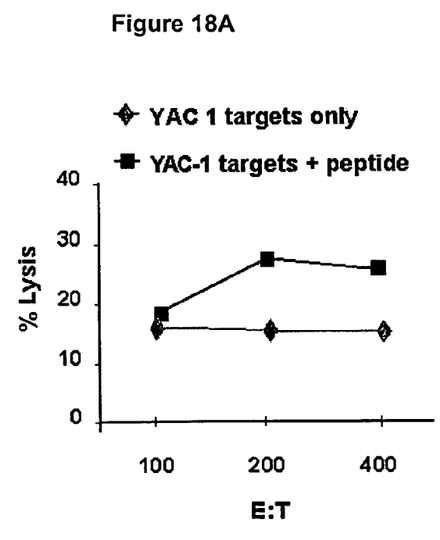
FIGS. 18A and 18B. Effect of normal BALB/c splenocytes with and without MUC1/sec peptide on lysis of YAC-1 (18A) and EL-4 (18B) target cells. Figure shows that MUC1/sec peptide activates normal BALB/c splenocytes to kill multiple targets.
Figure 18B:
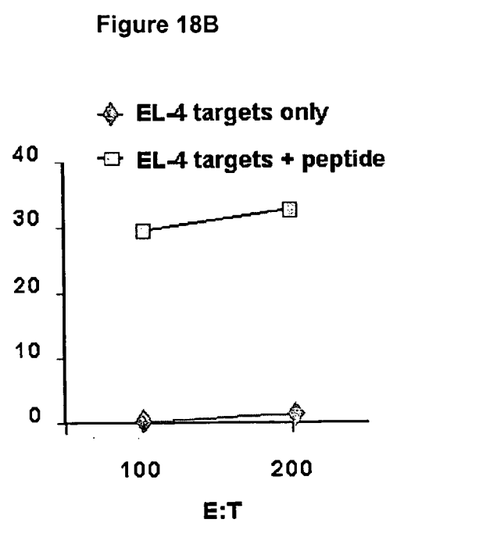
Figure 19A:
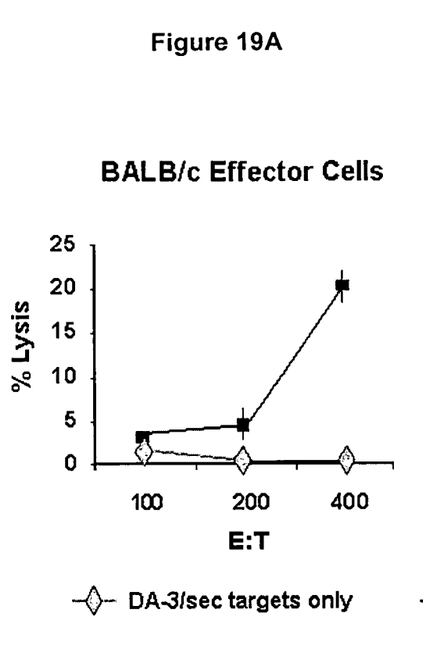
FIGS. 19A and 19B. Effect of normal splenocytes from different mouse strains with and without MUC1/sec peptide on lysis of DA-3/sec tumor cells. Figure shows that normal splenocytes kill DA-3/sec tumor cells in the presence of MUC1/sec peptide.
Figure 19B:
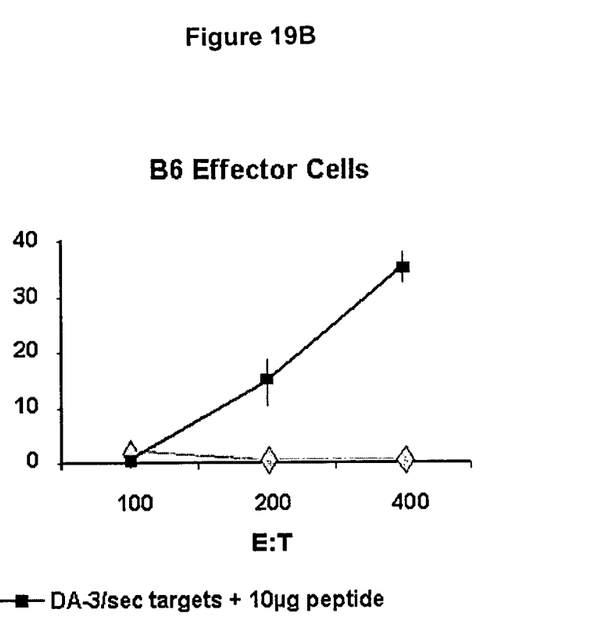

Other preliminary studies in our laboratory suggested that DA-3 cells transfected with the human MUC1 secreted form, but not the transmembrane form, stimulate effector cells to respond against DA-3/sec cells both in vivo and in vitro. As mentioned above, there is a unique 11 amino acid peptide present on the C-terminus of the MUC1/sec protein, but not on the MUC1/TM protein. A synthetic peptide was made corresponding to this peptide (termed "immunoenhancing peptide", or IEP), which when used in vaccination protocols, has been found to have protective effects against the DA3, DA3/neo, DA3-TM, K7 osteosarcoma, RENCA, and Lewis lung carcinoma cells. We investigated the possible effects of the peptide on the cytotoxicity reaction. We tested it on yet another tumor model, i.e. the D1-DMBA-3 mammary tumor bearing mice. The DA-3 cell line was originally derived from this tumor, which is routinely passaged in vivo in our laboratory in the syngeneic BALB/c mice. In FIG. 17, it can be seen that addition of the MUC1/sec unique peptide in vitro to splenocytes from either normal and D1-DMBA-3 tumor bearing mice for 5 days results in significant levels of cytotoxicity against the DA-3/sec tumor targets. Importantly, vaccination protocols similar to those described above gave significant protection against the growth of the D1-DMBA-3 tumor. The ability of this peptide to stimulate immune cells in a NK cell assay was tested. This assay was chosen based on the observation that the DA-3/sec tumor was suppressed during the initial stages of growth in the nude mice, suggesting that an innate immune component may be involved in the immediate reaction against DA-3/sec. Therefore, to test for immunomodulatory activity of the immunoenhancing peptide (IEP), BALB/c splenocytes were pretreated for 30-45 minutes with 10 μg IEP and subsequently, chromium-labeled YAC-1 or EL-4 targets were added in a 4-hour assay as previously described (11). As seen in FIG. 18, peptide addition resulted in an elevation of cytotoxic levels from normal splenocytes against the classic murine NK-target cells, YAC-1. Furthermore, EL-4 target cells, which are not susceptible to NK-type of cytotoxicity by normal splenic cells, were readily lysable by these effectors, when they were previously exposed to the immunoenhancing peptide. In other experiments we were able to activate splenic effector cells from normal BALB/c or C57 BL/6 (B6) mice to kill DA-3/sec target cells by previous exposure to the MUC1/sec unique peptide (FIG. 19).

EXAMPLE 14

It could be argued that the cytotoxicity observed is due to a direct toxic effect of the unique 11 amino acid peptide on the tumor cells. To test this possibility we added high levels of the IEP to several tumor targets in vitro and determined the cell viability after 4 days in culture. As seen in Table 3, such treatment with much higher peptide levels than those to which the cells are exposed in vivo, or in the effector cell mediated cytotoxicity assays caused no inhibition of growth or cytocidal activity against the tumor cells.

TABLE 3

Effect of Sec Peptide on In Vitro Tumor Growth

| TUMOR LINE | MEDIA ONLY | +KLH - Sec PEPTIDE[1] |
|---|---|---|
| DA-3 | $3.7 \times 10^6$ cells[2] | $3.5 \times 10^6$ cells |
| DA-3/neo | $3.9 \times 10^6$ cells | $4.0 \times 10^6$ cells |
| DA-3/TM | $3.1 \times 10^6$ cells | $3.0 \times 10^6$ cells |
| DA-3/sec | $2.9 \times 10^6$ cells | $3.1 \times 10^6$ cells |

[1]50 μg/well
[2]Total cells after 4 days in culture

CONCLUSIONS

The data disclosed herein indicate that transfection of a novel secreted isoform of the MUC1 gene (MUC1/sec) prevents the growth of an aggressive, immunogenic established tumor cell line in BALB/c mice. When used in vaccination protocols, it can afford protection against syngeneic tumors in a non-specific manner. A unique eleven amino acid peptide present in the MUC1/sec molecule is involved in the protective effects and when used in vaccination protocols it is capable of acting effectively against various tumor cell lines. The data also suggest that cytotoxicity by effector cells of the innate and/or adaptive immune system is involved in the observed results. Since the effects of this peptide are not restricted to a given type of tumor or mouse strain, it should be possible to use it alone and/or in combination with other immunomodulatory molecules against a wide variety of tumors. No toxicity has been detected in the animals injected with the peptide. The broad spectrum of action of this IEP may permit the use of this agent not only against tumors, but also against viral or bacterial diseases such as HIV, hepatitis B and C, and other microbial infections (e.g., tuberculosis), where an enhancement of the immune responses may have positive effects in the exposed individuals.

In describing preferred embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose.

The embodiments illustrated and discussed in the present specification are intended only to teach those skilled in the art the best way known to the inventors to make and use the invention, and should not be considered as limiting the scope of the present invention. The exemplified embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

All patents, published patent applications and other published references cited herein are hereby incorporated by reference. References are listed below for convenience.

REFERENCES

1. Ceriani R L, Thompson K E, Peterson J A, and Abrahams S: Surface differentiation antigens of human mammary epithelial cells carried on the human milk fat globule. Proc. Natl. Acad. Sci. (Wash) 74: 582-587, 1977.
2. Lloyd K O, Burchell J, Kudryashou V, Yin B W T, and Taylor-Papadimitriou J: Comparison of O-linked carbohydrate chains in MUC1 mucin from normal breast epithelial cell lines and breast carcinoma cell lines. J. Biol. Chem. 271: 33325-33334, 1996.
3. Smorodinsky N, Weiss M, Hartmann M-L, Baruch A, Harness E, Yaakobovitz M, Keydar I, and Wreschner D H: Detection of a secreted MUC1/SEC protein by MUC1 isoform specific monoclonal antibodies. Biochem. Biophys. Res. Comm. 228: 115-121, 1996.
4. Fu Y-X, Watson GA, Kasahara M, and Lopez D M: The role of tumor derived cytokines on the immune system of mice bearing mammary adenocarcinomas. I. Induction of regulatory macrophages by in vivo administration of rGM-CSF. J. Immunol. 146: 783-789, 1991.
5. Keydar I, Chou C S, Hareuveni M, Tsarfaty I, Sahar E, Selzer G, Chaitchik S, and Hizi A: Production and characterization of monoclonal antibodies identifying breast tumor associated antigens. Proc. Natl. Acad. Sci. (Wash.), 86:1362-1366, 1989.
6. Altschul S F, Gish W, Miller W, Myers E W, and Lipman D J: Basic local alignment search tool. J. Mol. Biol. 215: 403-410, 1990.
7. Nagata S and Golstein P: The FAS death receptor. Science 267: 1449-1456, 1995.
8. Podack E R, Olsen K J, Lowery D M, and Lichtenheld M: Structure and function of perforin. Curr. Top. Microbiol. Immunol. 140: 11-17, 1989.
9. Kataoka T, Shinohara N, Takayama H, Takaku K, Kondo S, Yonehara S, and Nagai K: Concanamycin A, a powerful tool for characterization and estimation of contributions of perforin- anad Fas-based lytic pathways in cell-mediated cytotoxicity. I. Immunol. 156: 3678-3686, 1996.
10. Herberman R B, Nunn M E, and Lavrin D H: Natural cytotoxic reactivity of mouse lymphoid cells against syngeneic and allogeneic tumors. I. Distribution of reactivity and specificity. Int. J. Cancer 16: 216-223, 1975.
11. Paul R, Padmanabhan R, and Lopez D M: Characterization of the effector cells mediating an "innocent bystander" cytotoxicity reaction induced by a syngeneic mammary adenocarcinoma in mice. Cancer Res. 44: 4480-4486, 1984.

---

---

What is claimed is:

1. A pharmaceutical composition comprising an isolated immunoenhancing peptide consisting of the amino acid sequence of SEQ ID NO: 1, an adjuvant, and isolated tumor cells, wherein said immunoenhancing peptide is bound to the adjuvant, and wherein said composition on administration to a mammal enhances innate or non-specific immune responses of said mammal against syngeneic tumors.

2. The composition of claim 1, wherein the adjuvant is selected from the group consisting of keyhole limpet hemocyanin (KLH), Interleukin-2 (IL-2), granulocyte-macrophage colony-stimulating factor (GM-CSF), and cytoxan.

3. The composition of claim 1 further comprising a pharmaceutically acceptable carrier or excipient.

4. The composition of claim 1, wherein said tumor cells are selected from the group consisting of mammary tumor cells, osteosarcoma cells, renal cell carcinoma cells, and Lewis lung carcinoma cells.

5. A vaccine comprising the composition of claim 1 and a pharmaceutically acceptable carrier or excipient.

* * * * *